United States Patent
Jia et al.

(10) Patent No.: US 11,072,817 B2
(45) Date of Patent: Jul. 27, 2021

(54) DETECTION OF DNA METHYLATION

(71) Applicant: ZYMO RESEARCH CORPORATION, Irvine, CA (US)

(72) Inventors: Xiyu Jia, Newport Beach, CA (US); Onyinyechi Chimaokereke, Tustin, CA (US); Lam Nguyen, Fountain Valley, CA (US)

(73) Assignee: ZYMO RESEARCH CORPORATION, Irvine, CA (US)

( * ) Notice: Subject to any disclaimer, the term of this patent is extended or adjusted under 35 U.S.C. 154(b) by 153 days.

(21) Appl. No.: 15/683,066

(22) Filed: Aug. 22, 2017

(65) Prior Publication Data

US 2018/0135113 A1 May 17, 2018

Related U.S. Application Data

(63) Continuation of application No. 13/581,971, filed as application No. PCT/US2011/026883 on Mar. 2, 2011, now abandoned.

(60) Provisional application No. 61/388,766, filed on Oct. 1, 2010, provisional application No. 61/383,408, filed on Sep. 16, 2010, provisional application No. 61/310,201, filed on Mar. 3, 2010.

(51) Int. Cl.
*C12P 19/34* (2006.01)
*C12Q 1/6827* (2018.01)

(52) U.S. Cl.
CPC .................. *C12Q 1/6827* (2013.01)

(58) Field of Classification Search
USPC ............ 435/6.1, 6.11, 6.12, 91.1, 91.2, 183; 436/94, 501; 536/23.1, 24.3, 24.33, 25.3
See application file for complete search history.

(56) References Cited

U.S. PATENT DOCUMENTS

| | | | |
|---|---|---|---|
| 5,489,507 | A | 2/1996 | Chehab |
| 2002/0045163 | A1 | 4/2002 | Salituro et al. |
| 2003/0219774 | A1 | 11/2003 | Sharma et al. |
| 2005/0095627 | A1 | 5/2005 | Kolman |
| 2005/0158739 | A1 | 7/2005 | Jeddeloh et al. |
| 2005/0202490 | A1 | 9/2005 | Makarov et al. |
| 2005/0272065 | A1 | 12/2005 | Lakey et al. |
| 2007/0231800 | A1 | 10/2007 | Roberts |
| 2008/0081338 | A1 | 4/2008 | Lo |
| 2009/0111707 | A1 | 4/2009 | Foekens |
| 2010/0015622 | A1 | 1/2010 | Hanna |
| 2010/0083407 | A1 | 4/2010 | Feldmann et al. |
| 2012/0003634 | A1 | 1/2012 | Frunkin et al. |

FOREIGN PATENT DOCUMENTS

| | | |
|---|---|---|
| WO | WO 2005/090607 | 9/2005 |
| WO | WO 2011/070441 | 6/2011 |
| WO | WO 2011/101728 | 8/2011 |

OTHER PUBLICATIONS

Extended European Search Report issued in European Application No. 11751298.8, dated Aug. 6, 2013.
Holemon et al., "MethylScreen: DNA methylation density monitoring using quantitative PCR", Biotechniques, 43(5):683-693, 2007.
International Preliminary Report on Patentability issued in International Application No. PCT/US11/26883, dated Sep. 13, 2012.
International Search Report and Written Opinion issued in International Application No. PCT/US11/26883, dated Apr. 26, 2011.
Kellogg et al., "TaqStart Antibody: 'hot start' PCR facilitated by a neutralizing monoclonal antibody directed against Taq DNA polymerase", Biotechniques, 16(6): 1134-1137, 1994 (Abstract only).
Obayashi et al., "Enzymatic synthesis of labeled DNA by PCR using new fluorescent thymidine nucleotide analogue and superthermophilic KOD dash DNA polymerase", Bioorg Med Chem Lett., 12(8): 1167-1170, 2002. (Abstract only).
Singler-Sam et al., A quantative HpaII-PCR assay to measure methylation of DNA from a small number off cells. Nucleic Acids Research, 18, 687, 1990.
Von Kanel et al., "Quantitative 1-step DNA methylation analysis with native genomic DNA as template", Clinical Chemistry, 56(7): 1098-1106, 2010.
Walker, et al., Isothermal in vitro amplification of DNA by a restriction enzyme/DNA polymerase system. Proc. Natl. Acad. Sci. USA, 89, 392-396, 1992.

*Primary Examiner* — Frank W Lu
(74) *Attorney, Agent, or Firm* — Parker Highlander PLLC

(57) ABSTRACT

In a first aspect, the invention concerns a method for detecting or quantifying DNA methylation at a locus. In one embodiment, a methylation-sensitive endonuclease is formulated together with a polymerase enzyme in an appropriate reaction mixture such that amplification of DNA occurs in a methylation specific manor. Quantitative DNA amplification at selected loci can be used to determine the level of methylation. Kits and reagents for performing such methods are also provided.

14 Claims, 6 Drawing Sheets
Specification includes a Sequence Listing.

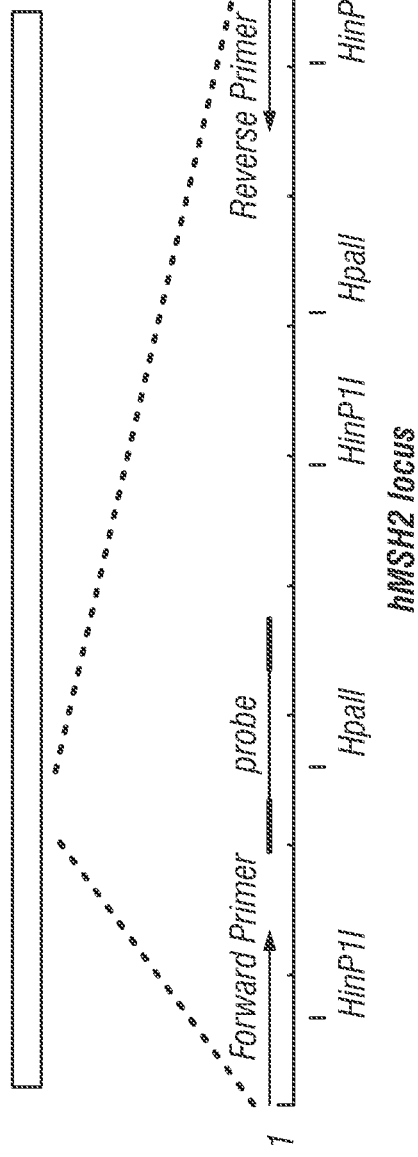
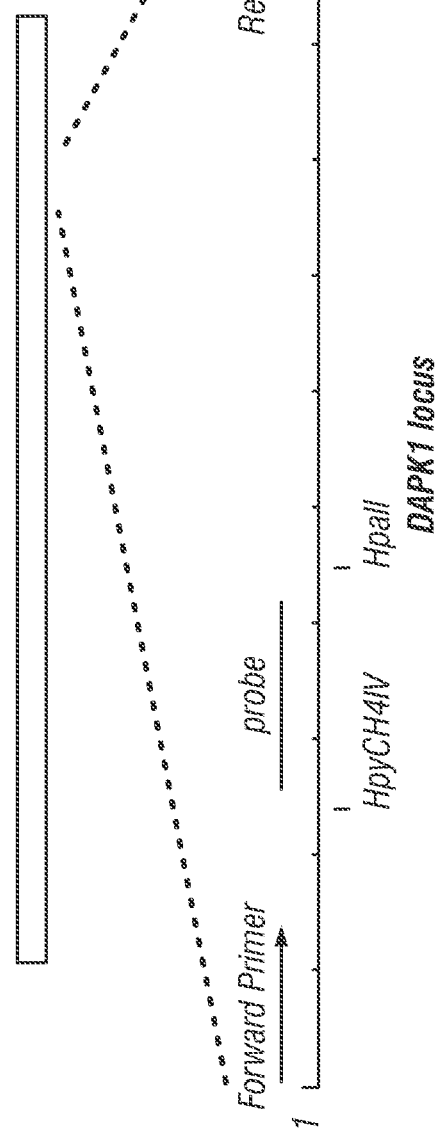

DETECTION OF DNA METHYLATION

REFERENCE TO RELATED APPLICATIONS

This application is a continuation of U.S. application Ser. No. 13/581,971, filed Nov. 21, 2012, as a national phase application under 35 U.S.C. § 371 of International Patent Application No. PCT/US2011/026883, filed Mar. 2, 2011, which claims the benefit of U.S. Provisional Application Nos. 61/310,201 filed Mar. 3, 2010; 61/383,408 filed Sep. 16, 2010; and 61/388,766 filed Oct. 1, 2010, all herein incorporated by reference in their entirety.

INCORPORATION OF SEQUENCE LISTING

The sequence listing that is contained in the file named "ZYMOP0005USC1_ST25.txt", which is 3 KB (as measured in Microsoft Windows®) and was created on Aug. 22, 2017, is filed herewith by electronic submission and is incorporated by reference herein.

FIELD OF THE INVENTION

The present invention generally relates to molecular biology. More specifically, the invention relates to methods and compositions for genomic DNA methylation analysis.

DESCRIPTION OF THE RELATED ART

Epigenetic modifications are regarded as fundamental elements in gene expression regulation. DNA methylation, one such modification, plays crucial roles in widespread biological phenomena including host defense in bacteria and cell cycle regulation, gene imprinting, embryonic development and X-chromosome inactivation in mammals. Aberrant DNA methylation patterns in gene promoters are closely associated with perturbations in gene expression and have recently been indicated as leading cause of human cancers (Jones and Laird, 1999).

The field of epigenetics has grown exponentially in the scientific community as irregularities with gene expression due to abnormal DNA methylation is the leading cause in human cancer types. DNA methylation involves the chemical addition of a methyl group to the 5' carbon position on the cytosine pyrimidine ring. Most DNA methylation occurs within CpG islands which are commonly found in the promoter region of a gene. Thus, this form of post modification of DNA acts as communicative signal for activation or inactivation of certain gene expression throughout various cell types.

Current methods to analyze DNA methylation status includes Me-DIP, HPLC, microarrays, and mass spectrometry, all of which use relatively expensive or hard to obtain machinery that may inhibit further research work. The most common method for DNA methylation analysis involves bisulfite treatment, in which unmethylated cytosines are converted to uracil while methylated cytosines remain unchanged, followed by downstream amplification and sequencing. However, bisulfite treatment is labor intensive and complicated to perform.

SUMMARY

In a first aspect the invention provides a method for detecting methylation status of a DNA sequence in a DNA sample comprising (i) contacting a DNA sample with a reaction mixture comprising a methylation-sensitive endonuclease (MSE), a DNA polymerase, oligonucleotide primers flanking the DNA sequence and a buffer formulated to facilitate activity of the MSE and the DNA polymerase; (ii) incubating the sample under conditions permissive for DNA cleavage by the MSE; (iii) incubating the sample under conditions permissive for DNA polymerization (i.e., conditions permissive for polymerase chain reaction (PCR)); and (iv) detecting DNA amplification wherein DNA amplification is indicative of methylation status of the DNA sequence in the DNA sample. In certain embodiments, the reaction mixture volume is not adjusted during steps (ii)-(iii) of the method (e.g., no additional components are added to the reaction mixture). In a further embodiment, the incubation steps (ii-iii) are automated, such as by the use of a thermal cycler.

In a further aspect, a method according to the invention may be defined as method for quantitating the proportion of DNA methylation in a DNA sequence or at a specific DNA position. Thus, in certain embodiments, the step (iii) comprises incubating the sample in conditions permissive for quantitative PCR (qPCR). Following qPCR the amount to amplified DNA can be determined and used to determine the proportion of methylation in the DNA sequence of the sample. For example, quantitating methylation in the DNA sample may comprise comparing the amount of DNA amplification to an amplification standard. An amplification standard may, for example, be a DNA sample with a known proportion of methylation. In further embodiments, the amplification standard is obtained by subjecting a portion of a DNA sample to a method according to the invention wherein the MSE is substantially absent or inactive, thereby determining the amount of DNA amplification that occurs when no methylation-sensitive DNA cleavage occurs.

Methods for quantitating the proportion of methylated DNA based on the amount of DNA amplification are further detailed below. In one method, for instance, the proportion of DNA methylation is determined from a change in the cycle threshold (Ct) value obtained from the DNA amplification as compared to an amplification standard. For example, in one embodiment wherein the MSE or MSE mixture exhibits reduced cleavage in the presence of DNA methylation that overlaps the enzyme recognition site(s) methylation percent=$100 \times 2^{-\Delta Ct}$ where $\Delta Ct=Ct$ obtained from a sample incubated with active MSE minus the Ct obtained from a sample incubated in a reaction mixture without active MSE. In embodiments wherein the MSE or MSE mixture exhibits increased cleavage in the presence of DNA methylation that overlaps the enzyme recognition site(s) methylation (%)=$100-(100 \times 2^{-\Delta Ct})$.

In certain aspects, a method for quantifying site-specific DNA methylation prevalence in a genomic DNA sample comprises (a) digesting a portion (e.g., half) of the DNA sample with MSE to specifically cleave methylated or non-methylated DNA; (b) incubating another portion (e.g., the second half) of the DNA sample with inactivated MSE; (c) amplifying the MSE-treated DNA from both samples using a DNA polymerase and oligonucleotide primers in the presence of an oligonucleotide probe or dye to produce amplified samples; and (d) determining the methylation status be measuring Ct values for the amplified samples. Quantification of site-specific DNA methylation may be accomplished, for example, by comparing the Ct values obtained from the samples to established Ct values correlated to percent DNA methylation.

In a further embodiment, the invention provides a reaction mixture comprising at least one MSE, a DNA polymerase and a buffer formulated to facilitate activity of the methylation-sensitive DNA endonuclease and the DNA polymerase. In certain aspects, a reaction mixture is formulated such that the MSE and polymerase may be frozen without substantial loss of activity. In a further aspect, the reaction mixture is provided as a kit of separately packaged components along with instructions for formulating a complete reaction mixture from the components. As further detailed herein a reaction mixture according to the invention may further comprise one or more additional MSEs, free nucleotides, salts, preservatives, one or more oligonucleotide probes, one or more oligonucleotide primers and/or appropriate labels and dyes.

In still a further embodiment, a kit is provided comprising one or more vials comprising a reaction mixture according to the invention. Such a kit may further comprise one more additional components such as a reaction mixture wherein the MSE component is absent or inactive, an instruction pamphlet for methylation analysis, one or more oligonucleotide primers, a DNA sample or a DNA amplification standard.

In certain aspects, a reaction mixture comprises an oligonucleotide probe that binds to a DNA sequence in a sample (e.g., in a region flanked by oligonucleotide primers). In further embodiments, oligonucleotide primers or probes comprise a label. Alternatively or additionally, a reaction mixture may comprise a label that binds to double stranded DNA, such as SYBR® Green, a SYTO dye (e.g., SYTO® 9) or free nucleotides that are labeled. Useful labels include, but are not limited to, fluorescent labels, radioactive labels, sequence labels, enzymatic labels and affinity labels. The presence of labeled (e.g., fluorescent labeled) continuants in the reaction mixture may be used to facilitate detection and quantification of DNA amplification.

In one embodiment a MSE comprises an enzyme having reduced activity on methylated DNA substrates. Such enzymes may be naturally occurring or an engineered recombinant enzyme. Examples of such MSEs for use according to the invention include, but are not limited to, AccII, AciI, HpaII, HinP1I, HpyCH4IV, AatII, AclI, AfeI, AgeI, AscI, AsiSI, AvaI, BmgBI, BsaAI, BsaHI, BsiEI, BsiWI, BsmBI, BspDI, BstBI, ClaI, EagI, FauI, FnuDII, FseI, FspI, HaeII, HgaI, HhaI, Hpy99I, KasI, MluI, NaeI, NarI, NgoMIV, NotI, NruI, PaeR7I, PmlI, PvuI, RsrII, SacII, SalI, SfoI, SgrAI, SmaI, SnaBI or ZraI. In certain cases, the MSE is an endonuclease which recognizes a 4-base-pair sequence (e.g., a 4-based pair sequence comprising a CpG dinucleotide sequence). For example, an AciI, AccII, HpaII, Hinp1I or HpyCH4IV enzyme or a combination thereof can be used.

In second embodiment a MSE comprises an enzyme having increased activity on methylated DNA substrates (e.g., a methylation-dependent endonuclease). Such enzymes may be naturally occurring or an engineered recombinant enzyme. Examples of such MSEs for use according to the invention include, but are not limited to, BisI, GlaI, McrBC or a mixture thereof.

In some cases, disclosed methods involve cleaving the genomic DNA with at least 2, at least 3, at least 4 or more MSEs. Accordingly reaction mixtures may comprise 2, 3, 4 or more MSEs. In certain embodiments a MSE for use according to the invention is an MSE that can be heat inactivated, such as an enzyme that retains less than about 10%, 5%, 2% or 1% of its activity after heat inactivation.

In certain aspects, methods and compositions according to the invention involve DNA polymerase enzymes. In one embodiment the DNA polymerase enzyme is an enzyme that thermal stable, such as taq. Methods and reaction mixtures disclosed here may further comprise molecules that modulate DNA polymerase activity or DNA polymerase enzymes that have been modified for "hot start" activity. For example, a reaction mixture may comprise a molecule (e.g., a DNA polymerase-binding antibody) that inhibits DNA polymerase activity during MSE cleavage of a DNA sample. Such DNA polymerase systems are also commonly referred to as "hot start" systems.

A DNA sample for use according to the invention may be any sample that comprises DNA that is potentially methylated. For example, the sample may comprise genomic DNA (e.g., mammalian genomic DNA), such as human genomic DNA. A DNA sample can be obtained from a variety of sources such as from a human subject or from a cell line or tissue bank. DNA from a patient or subject may be isolated from, for example, a blood sample, a tissue biopsy sample, a urine sample or a saliva sample.

Embodiments discussed in the context of a methods and/or composition of the invention may be employed with respect to any other method or composition described herein. Thus, an embodiment pertaining to one method or composition may be applied to other methods and compositions of the invention as well.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings are part of the present specification and are included to further demonstrate certain aspects of the present invention. The invention may be better understood by reference to the drawings in combination with the detailed description of specific embodiments presented herein.

FIG. 2A-B: Exemplary genomic loci for methylation analysis. FIG. 2A, the hMSH2 locus includes three Hinp1I sites and two HpaII sites. Forward primers hybridize to a Hinp1I site, the probe to a HpaII site and the reverse primers to a Hinp1I site. FIG. 2B, the DAPK1 locus encompasses one HpyCH4IV and one HpaII site.

DETAILED DESCRIPTION OF THE INVENTION

Figure 1:
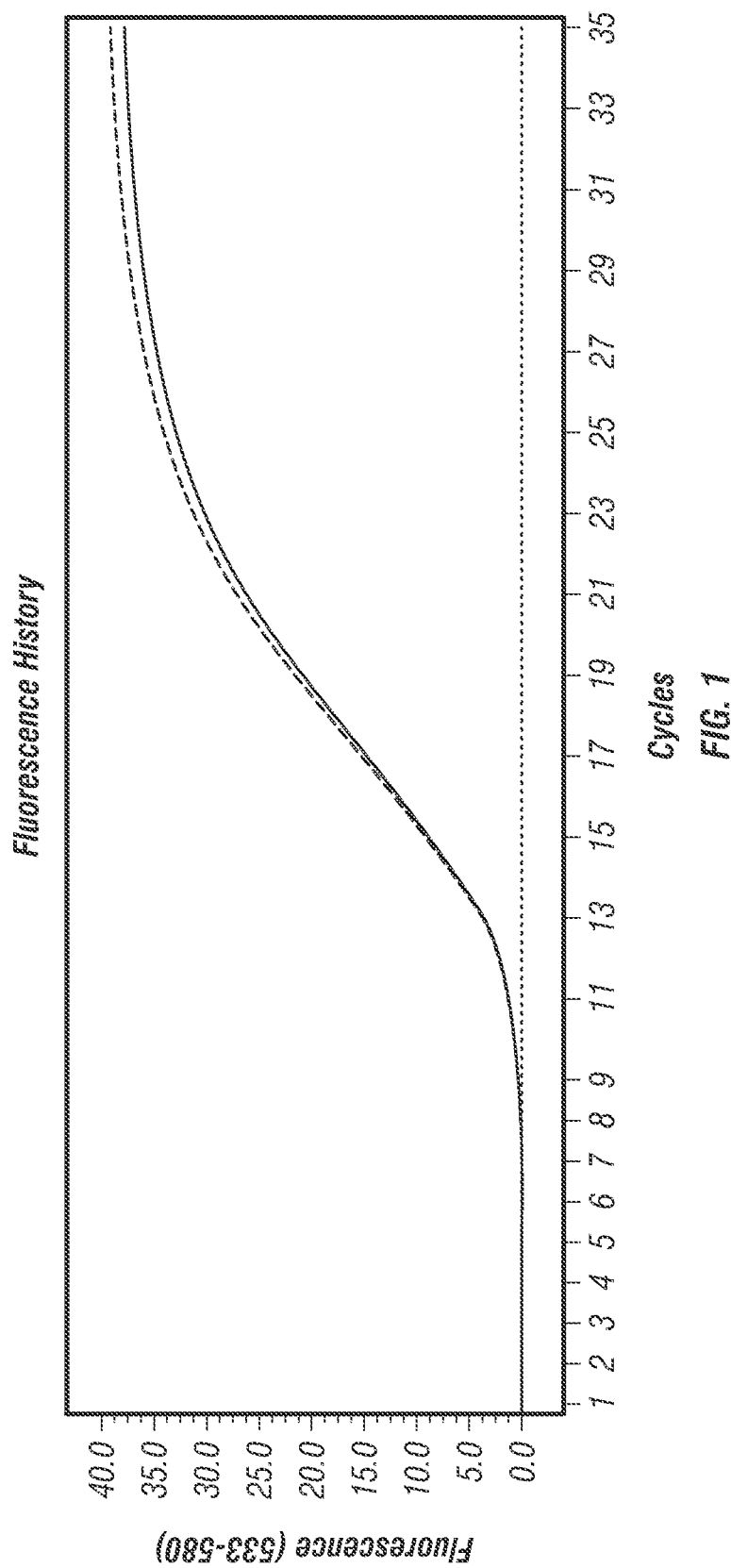
FIG. 1: One-step MSE-qPCR selectively amplifies methylated DNA. 5 ng of fully methylated and non-methylated pUC19 was subjected to one-step MSE-qPCR. Methylated pUC19 (top two curves) and non-methylated pUC19 (bottom line) were differentially amplified.

The following is a detailed description of the invention provided to aid those skilled in the art in practicing the present invention. Those of ordinary skill in the art may make modifications and variations in the embodiments described herein without departing from the spirit or scope of the present invention.

DNA methylation plays a central role in widespread biological phenomena. Current methods used to evaluate DNA methylation such as bisulfite sequencing and Methylation Specific PCR present a number of problems as they are expensive, lengthy and involve multiple steps that increase chances of contamination. In contrast, the invention provides single reaction system for rapid and accurate DNA methylation quantification. The method exploits the specificity of MSE to digest methylated or unmethylated CpG dinucleotides juxtaposed to real-time PCR for the selective amplification of methylated DNA. Thus, multiple steps and reactions are integrated into one simple step. Advantages offered by this new system include decreased opportunity for contamination and rapid and accurate DNA methylation percentage quantification. The disclosed method is demonstrated to selectively amplify methylated DNA and accurately measure methylation profiles of known DNA methylated standards when MSEs that have decreased activity at methylated DNA positions are used. Methylation percentages of blind controls determined by the method closely coincided with actual methylation percentages. The assay has also proven to be a cost-effective for accurate region-specific methylation status quantification and will be a valuable tool in research and diagnostics.

Methods for quantitating the proportion of methylated DNA based on the amount of DNA amplification are further detailed below. For example, in one method the proportion of DNA methylation is determined from the change in the cycle threshold (Ct) value obtained from the DNA amplification. By using the principle that each successive round of PCR amplification results in approximately a 2-fold increase in the amount of product. Thus, a ΔCt of 1 indicates that 50% template has been cleaved. The relationship between ΔCt and percent methylation is expressed using the formula Methylation (%)=$100 \times 2^{-\Delta Ct}$ where: ΔCt=Ct active MSE master mix–inactive MSE master mix (in the case of an MSE that has reduced activity at methylated sites); or ΔCt=inactive MSE master mix–Ct active MSE master mix (in the case of an MSE that is methylation dependent).

I. General Protocol

An illustrative and non-limiting protocol for methylation analysis according to the invention is exemplified below.

1. Contact a DNA sample with a reaction mixture for MSE cleavage and qPCR. A reaction mixture may be formulated with a MSE, a DNA polymerase (e.g., a theremophilic DNA polymerase or a hot-start DNA polymerase system), oligonucleotide primers flanking the DNA sequence, dNTPs and a buffer formulated to facilitate activity of the MSE and the DNA polymerase. Reaction mixtures may additionally comprise a DNA binding label that can be used to detect the presence of dsDNA such as SYTO 9™. Salt concentrations in the reaction mixture will vary depending upon the MSE and polymerase used. For example, a 2× reaction mixture may comprise about 7.5 mM $MgCl_2$.

An MSE for use in the reaction mixture may be a naturally occurring or engineered enzyme. For example, the MSE can be an enzyme blocked by DNA methylation, such as one or more of AatII, AccIII, AciI, AfaI, AgeI, AhaII, Alw26I, Alw44I, ApaLI, ApyI, AscI, Asp718I, AvaI, AvaII, Bme216I, BsaAI, BsaHI, BscFI, BsiMI, BsmAI, BsiEI, BsiWI, BsoFI, Bsp105I, Bsp119I, BspDI, BspEI, BspHI, BspKT6I, BspMII, BspRI, BspT104I, BsrFI, BssHII, BstBI, BstEIII, BstUI, BsuFI, BsuRI, Cad, CboI, CbrI, CceI, Cfr10I, ClaI, Csp68KII, Csp45I, CtyI, CviAI, CviSIII, DpnII, EagI, Ecl136II, Eco47I, Eco47III, EcoRII, EcoT22I, EheI, Esp3I, Fnu4HI, FseI, FspI, Fsp4HI, GsaI, HaeII, HaeIII, HgaI, HhaI, HinP1I, HpaII, HpyAIII, ItaI, KasI, Kpn2I, LlaAI, LlaKR2I, MboI, MflI, MluI, MmeII, MroI, MspI, MstII, MthTI, NaeI, NarI, NciAI, NdeII, NgoMIV, NgoPII, NgoS II, NlaIII, NlaIV, NotI, NruI, NspV PmeI, PmlI, Psp1406I, PvuI, RalF40I, RsaI, RspXI, RsrII, SacII, SalI, Sau3AI, SexAI, SfoI, SfuI, SmaI, SnaBI, SolI, SpoI, SspRFI, Sth368I, TaiI, TaqI, TfiI, TthHB8I, VpaK11BI, or XhoI. In another example, the MSE can be an enzyme that cleaves DNA only in the presence methylation such as BisI, GlaI, or McrBC (see, e.g., Chernukin et al., 2006; Russian Patent No. 2322494; and Sutherland et al., 1992, each incorporated herein by reference).

DNA samples may be obtained from a variety of sources, as further detailed herein. In certain cases, a plurality of DNA samples are analyzed in parallel. Samples for parallel analysis may include a DNA standard having a known level of methylation. Likewise, a plurality of different oligonucleotide probes may be employed to determine methylation status at multiple regions within a DNA sample.

2. Incubate the sample under conditions permissive for DNA cleavage by the MSE. The buffer and temperature conditions for MSE cleavage may be adjusted based on the specific MSE enzymes used and as further detailed herein. For example, using AccII, HpaII and/or HpyCH4IV involves an incubation at 37° C. In the case of a McrBC and/or GlaI the incubation would also be at about 37° C.

3. Incubate the sample under conditions permissive for DNA polymerization. Methods and reagents for qPCR have been previously described and can be modified as described herein for quantitative amplification of a DNA sample. In certain aspects, samples are incubated in thermocycler and subjected to 25-40 rounds of amplification using temperatures to facilitate denaturation of the primers; annealing of the primers to sample DNA and elongation of intact sample DNA.

4. Detect DNA amplification. Methods for detecting DNA amplification from qPCR are well known in the art and exemplified herein. For example, a fluorescent dye that binds to dsDNA can be detected. In this case, an increase in fluorescence is indicative of DNA amplification. Likewise labeled DNA probes may be used to detect amplification. In certain aspects, multiple labels or dyes may be included in single reaction.

5. Determine the proportion of methylation in a DNA sample. DNA amplification detected in step (4) may be used to determine the Ct for each test and control reaction (comprising an inactive MSE). Methylation percentage in the DNA flanked by amplification primers can then be determined using the formula: methylation $\% = 100 \times 2^{-\Delta Ct}$.

II. Genomic Dna and Samples

Exemplary eukaryotic genomic DNA that can be used in a method of the invention includes, without limitation, mammal DNA such as a rodent, mouse, rat, rabbit, guinea pig, ungulate, horse, sheep, pig, goat, cow, cat, dog, primate, human or non-human primate. Plant DNA may also be analyzed according to the invention. For example, DNA from *Arabidopsis thaliana*, maize, sorghum, oat, wheat, rice, canola, or soybean may be analyzed. It is further contemplated that genomic DNA from other organisms such as algae, a nematodes, insects (e.g., *Drosophila melanogaster*, mosquito, fruit fly, honey bee or spider), fish, reptiles, amphibians and yeast may be analyzed.

As indicated above, genomic DNA can be isolated from one or more cells, bodily fluids or tissues. An array of methods can be used to isolate genomic DNA from samples such as blood, sweat, tears, lymph, urine, saliva, semen, cerebrospinal fluid, feces or amniotic fluid. Genomic DNA can also be obtained from one or more cell or tissue in primary culture, in a propagated cell line, a fixed archival sample, forensic sample or archeological sample. Methods for isolating genomic DNA from a cell, fluid or tissue are well known in the art (see, e.g., Sambrook et al., 2001).

Exemplary cell types from which genomic DNA can be obtained in a method of the invention include, a blood cell such as a B lymphocyte, T lymphocyte, leukocyte, erythrocyte, macrophage, or neutrophil; a muscle cell such as a skeletal cell, smooth muscle cell or cardiac muscle cell; germ cell such as a sperm or egg; epithelial cell; connective tissue cell such as an adipocyte, fibroblast or osteoblast; neuron; astrocyte; stromal cell; kidney cell; pancreatic cell; liver cell; or keratinocyte. A cell from which genomic DNA is obtained can be at a particular developmental level including, for example, a hematopoietic stem cell or a cell that arises from a hematopoietic stem cell such as a red blood cell, B lymphocyte, T lymphocyte, natural killer cell, neutrophil, basophil, eosinophil, monocyte, macrophage, or platelet. Other cells include a bone marrow stromal cell (mesenchymal stem cell) or a cell that develops therefrom such as a bone cell (osteocyte), cartilage cells (chondrocyte), fat cell (adipocyte), or other kinds of connective tissue cells such as one found in tendons; neural stem cell or a cell it gives rise to including, for example, a nerve cells (neuron), astrocyte or oligodendrocyte; epithelial stem cell or a cell that arises from an epithelial stem cell such as an absorptive cell, goblet cell, Paneth cell, or enteroendocrine cell; skin stem cell; epidermal stem cell; or follicular stem cell. Generally any type of stem cell can be used including, without limitation, an embryonic stem cell, adult stem cell, totipotent stem cell or pluripotent stem cell.

A cell from which a genomic DNA sample is obtained for use in the invention can be a normal cell or a cell displaying one or more symptom of a particular disease or condition. Thus, a genomic DNA used in a method of the invention can be obtained from a cancer cell, neoplastic cell, apoptotic cell, senescent cell, necrotic cell, an autoimmune cell, a call comprising a heritable genetic disease or the like.

DNA for use according to the invention may be a standard or reference DNA sample. Such reference samples may comprise a known level of DNA methylation. For example, reference DNA samples may be DNA extracted from cells that lack one of more DNA methyltransferase enzyme and are essentially devoid of CpG methylation. In further aspects, a reference DNA sample may be treated with a DNA methyltransferase (e.g., M.SsssI methyltransferase) and therefore comprise methylation at essentially all CpG sites that can be methylated. For example, a standard DNA may be DNA isolated from the human cell line such as the HCT116 DKO cell line. In certain aspects, methods according to the invention involve the use of two for more standard DNA samples, such as DNA samples comprising essentially no CpG methylation and essentially complete CpG methylation.

III. Reagents and Kits

The kits may comprise suitably aliquoted reagents of the present invention, such as a control premix (comprising one or more inactivated MSE(s)) and test premix (comprising one or more active MSE(s)). Control and test premix reagents comprise all of the components required for efficient MSE DNA cleavage and for qPCR. For example, the premix may comprise one, two, three or more MSEs, a DNA polymerase, free nucleotides, and salt/buffer system formulated to maximize activity of the polymerase and MSE enzymes. Premix reagents may also comprise a label that can be used to quantify PCR amplification in the sample. For example, the label may be a fluorescent label that binds to amplified dsDNA or a nucleic acid probe that specifically binds to amplified DNA. Dyes for used in reagents include for example a SYTO nucleic acid binding dye available from Life Technologies Corporation. See e.g., U.S. Pat. Nos. 5,436,134 and 5,658,751, incorporated herein by reference. In certain aspects, a premix reaction may also comprise oligonucleotide primers; however, such primers may also be packaged separately. Premix reactions must be carefully formulated to ensure that they are free of unwanted DNA as well as nonspecific DNase activity.

Additional components that may be included in a kit according to the invention include, but are not limited to, oligonucleotide primers, reference DNA samples (e.g., methylated and non-methylated reference samples), distilled water, probes, dyes, sample vials and instructions for performing methylation assays. In certain further aspects, reagents for DNA isolation, DNA purification and/or DNA clean-up may also be included in a kit.

The components of the kits may be packaged either in aqueous media or in lyophilized form. The container means of the kits will generally include at least one vial, test tube, flask, bottle, syringe or other container means, into which a component may be placed, and preferably, suitably aliquoted. Where there is more than one component in the kit, the kit also will generally contain a second, third or other additional container into which the additional components may be separately placed. However, various combinations of components may be comprised in a vial. The kits of the present invention also will typically include a means for containing reagent containers in close confinement for commercial sale. Such containers may include cardboard containers or injection or blow-molded plastic containers into which the desired vials are retained.

When the components of the kit are provided in one or more liquid solutions, the liquid solution is an aqueous solution, with a sterile aqueous solution being preferred.

However, the components of the kit may be provided as dried powder(s). When reagents and/or components are provided as a dry powder, the powder can be reconstituted by the addition of a suitable solvent. It is envisioned that the solvent may also be provided in another container means.

IV. Definitions

Endonuclease: As used herein the term "endonuclease" refers to an enzyme that cleaves nucleic acid molecules at an internal position. The terms "endonuclease" and "restriction endonuclease" are used interchangeably. Accordingly, the term "methylation-sensitive endonuclease (MSE)" is used interchangeably with ""methylation-sensitive restriction enzyme (MSRE)."

Methylation-sensitive endonuclease: As used herein the term "methylation-sensitive endonuclease" or "MSE" refers to endonuclease enzymes that have increased or decreased activity at DNA sites that include one or more methylated positions. Accordingly, in one embodiment, an MSE comprises reduced or blocked activity when DNA methylation is present. In a second embodiment, a MSE comprises increased activity when methylation is present (e.g., a methylation-dependent endonuclease).

V. Examples

The following examples are included to demonstrate certain embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

Example 1

One-Step DNA Methylation Quantification

Genomic DNA used in the study was from Zymo Research's Human Methylated and Non-methylated DNA set derived from HCT116 DKO cells. The DNA has a low level of DNA methylation (<5%) and can be used as a negative control for DNA methylation analysis. The Human HCT116 DKO methylated DNA is purified HCT116 DKO DNA that has been enzymatically methylated at all cytosine positions comprising CG dinucleotides by M.SssI methyltransferase 2 (EC 2.1.1.37;) and can be used as a positive control for DNA methylation analysis.

Primers were designed to flank MSE restriction sites and generate amplicons in the range of from about 50 to about 200 bp.

The forward primer, reverse primer and probe for HMSH2 locus respectively were 5'-GCTTCGTGCGCTTCTTTCAG-3' (SEQ ID NO: 1), 5'-CCGTGCGCCGTATAGAAGTC-3' (SEQ ID NO: 2) and 5'FAM-CATGCCGGAGAAGCCGACCAC-BHQ3' (SEQ ID NO: 3).

The forward primer, reverse primer and probe for DAPK1 locus respectively were; 5'-TCATGACCGTGTTCAGGCAGG-3' (SEQ ID NO: 4), 5'-ATGCATTTCCACAATCCAGGAGG-3' (SEQ ID NO: 5) and 5'FAM-ATTACTACGACACCGGCGAGGAACT-BHQ3' (SEQ ID NO: 6).

PCR amplification was initially performed on input DNA to determine optimum annealing temperature and minimal primer dimers. MSE digest and qPCR were integrated into carried a single step. Twenty nanograms of input DNA was added to the one-step MSE-qPCR master mix (1× ZymoTaq reaction buffer (commercially available from Zymo Research Corp.), 0.25 mM dNTPs, 0.04 U/mL ZymoTaq, 2 mM MgCl$_2$, 0.4 µM forward and reverse primers, 0.2 µM probe, 0.025 U/µl Hinp1I and 0.05 U/µl HpaII, AciI and HpyCH4IV) in a reaction volume of 25 µl. The samples were digested for 2 hr at 37° C. followed by real-time PCR amplification for 45 cycles. Cycle threshold (Ct) values were obtained from real-time PCR amplification. Each qPCR was performed in triplicate. For each reaction, a negative control was prepared by the use of inactivated MSEs (65° C. for 20 minutes) instead of active MSEs.

Percent DNA methylation was determined from the change in Ct value by using the principle that each successive round of PCR amplification results in approximately a 2-fold increase in the amount of product. Thus, a ΔCt of 1 indicates that 50% template has been cleaved. The relationship between ΔCt and percent methylation is expressed using the formula Methylation (%)=100×2$^{-\Delta Ct}$ where ΔCt=Ct active MSE master mix–inactive MSE master mix.

The correlation between actual methylation percentages and methylation percentages measured by the one-step MSE-qPCR system was examined using linear regression.

Figure 3A:
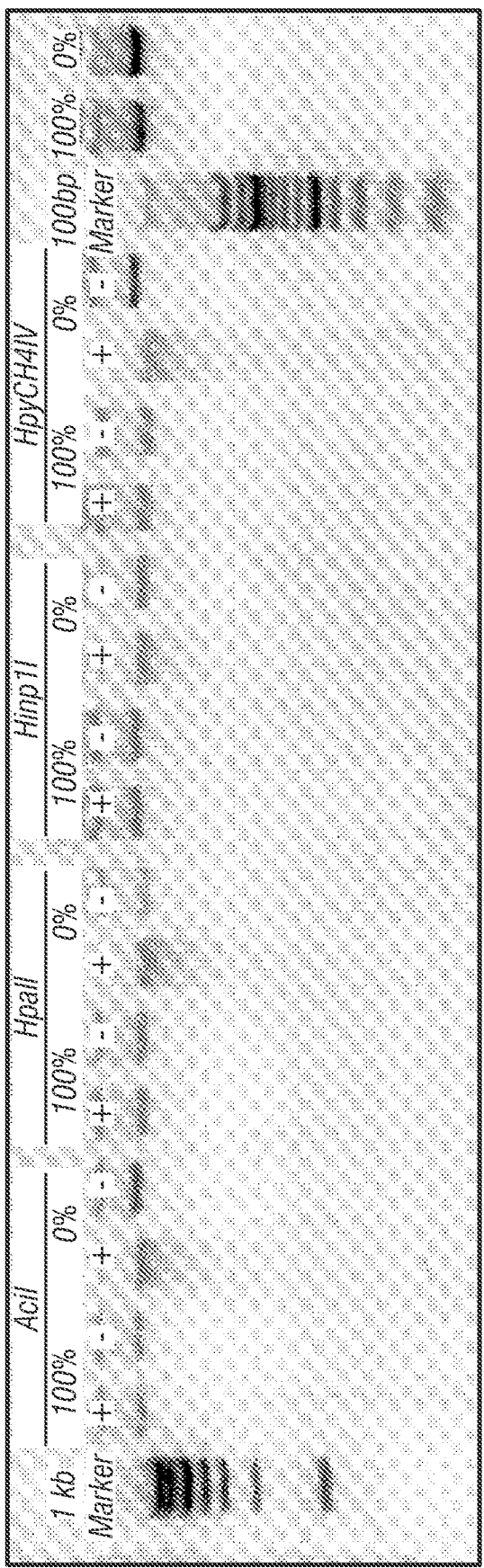
FIG. 3A-B: Digestion of fully and non-methylated DNA by one-step MSE-qPCR master mix is comparable to optimal buffer conditions. Fully methylated and non-methylated human DNA were digested in either 5 U AciI, Hinp1I or HpyCH4IV or 25 U HpaII for 2 hrs at 37° C. either under standard MSE buffer conditions (FIG. 3A) or using the one-step MSE-qPCR master mix (FIG. 3B).
Figure 3B:
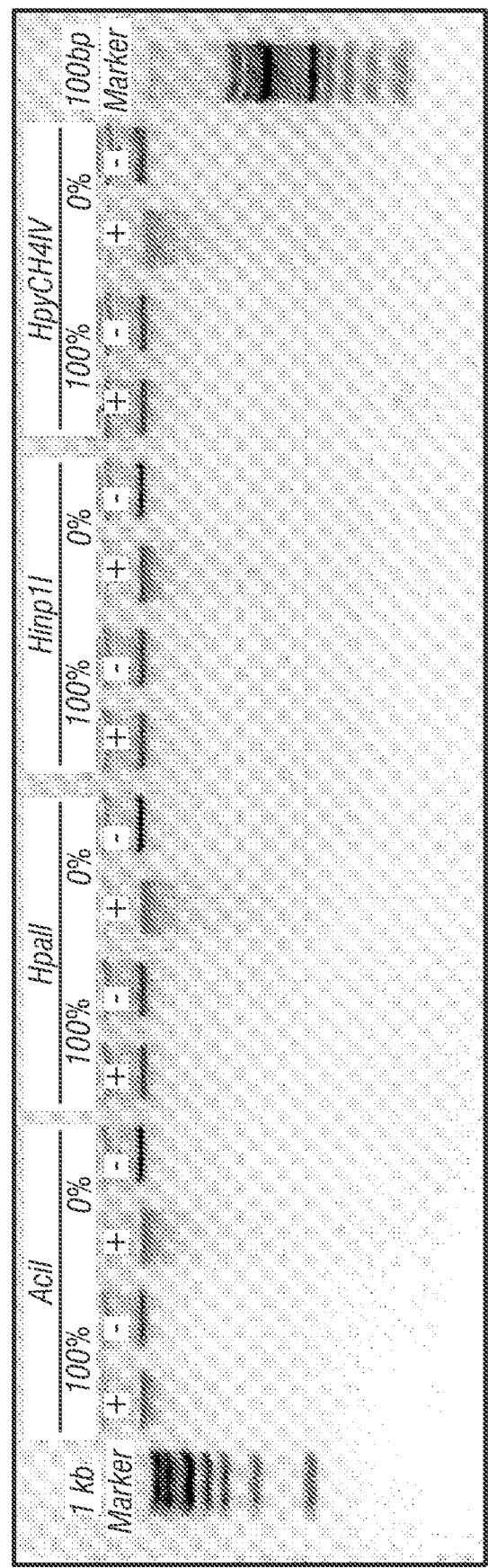

To validate the procedure outlined above, the ability of the one-step MSE-qPCR system to fully digest unmethylated DNA and selectively amplify methylated pUC19 DNA was examined (FIG. 1). The amplification curve clearly demonstrates the preferential amplification of methylated DNA. These data also suggests complete DNA digestion by the one-step MSE-qPCR method. To verify the ability of the one-step MSE-qPCR master mix to digest input DNA, 200 ng fully methylated and non-methylated human gDNA was subjected to MSE digest for 2 hours at 37° C. in a 25 µl final reaction volume either under standard NEB conditions or by the one-step MSE-qPCR master mix. Separation of digests by agarose gel electrophoresis confirmed the ability of the single-buffered one-step system to efficiently digest DNA (FIG. 3). Indeed, MSE digestion in the single MSE-qPCR master mix digested DNA as efficiently as the corresponding optimum NEB buffer.

Figure 4:
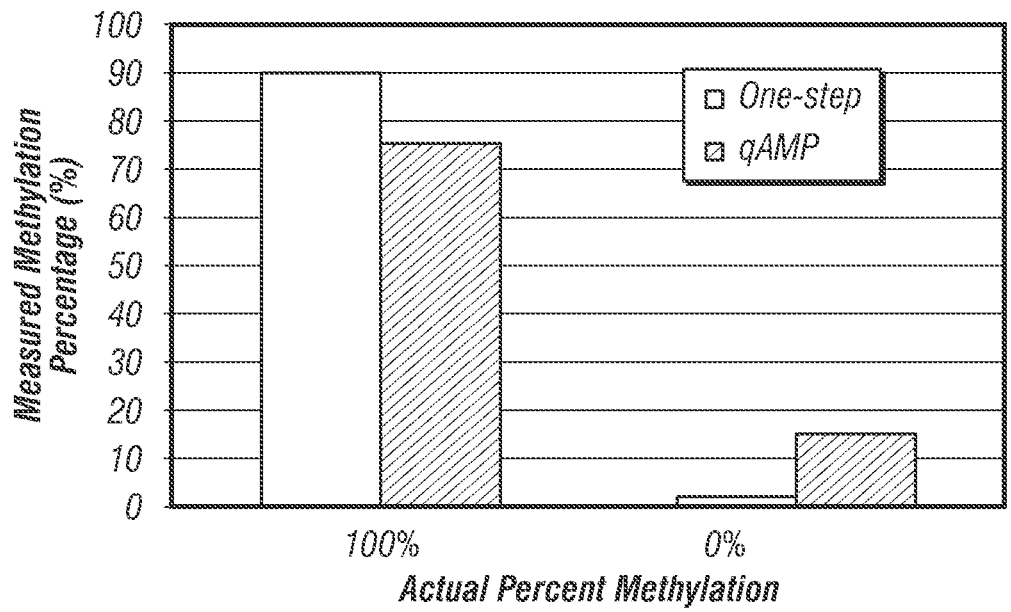
FIG. 4: Comparison of qAMP methylation values to one-step MSE-qPCR values. Fully methylated and non-methylated human genomic DNA was subjected to Hinp1I digestion and qPCR using either qAMP or the one-step MSE-qPCR method to ascertain the hMSH2 locus methylation status. Methylation percent values were calculated by applying ΔCt values to the established relationship.

The single-step MSE-qPCR procedure was further evaluated by comparing its measured methylation levels with methylation levels determined by traditional qAMP (Oakes et al., 2009). Percent methylation assessment of the hMSH2 locus (FIG. 2A) with fully and non-methylated human DNA by qAMP and the one-step master mix generated similar percent methylation values in both procedures (FIG. 4). Thus, region-specific, rapid DNA methylation quantification by the one-step MSE method is as accurate as the two day qAMP procedure.

Figure 5:
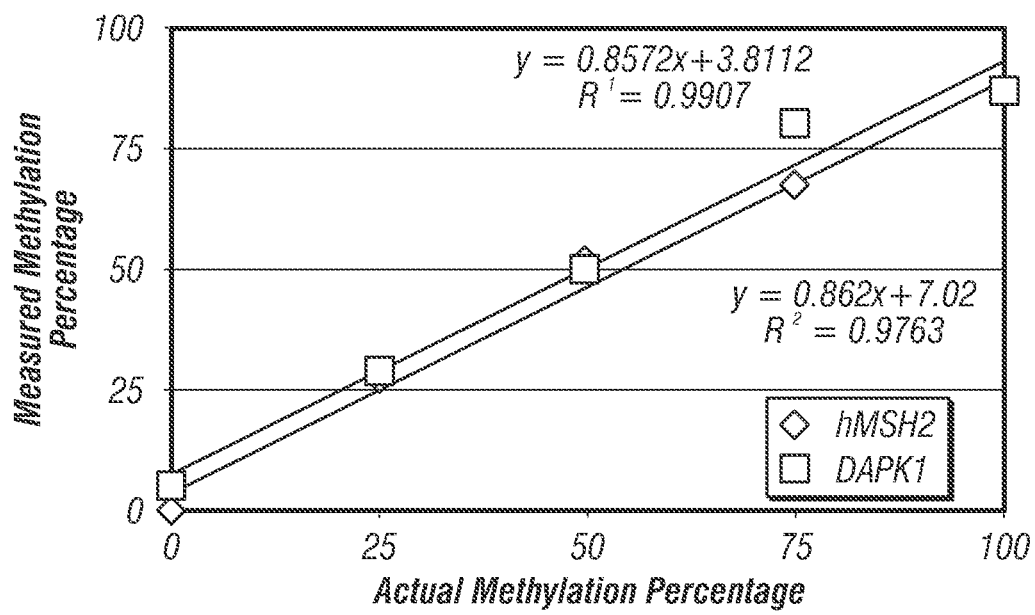
FIG. 5: Methylation values of standards using one-step quantification method coincide with actual methylation values. Human DNA standards with known methylation percentages were MSE-digested and amplified using the one-step MSE-qPCR method. Methylation percent values of all CpGs in the hMSH2 locus (diamonds) and DAPK1 locus (squares) were calculated by applying ΔCt values to the established relationship.

To further demonstrate the value of the one-step MSE-qPCR procedure, the correlation between true and measured methylation percentages in two loci, hSMH2 and DAPK1, were assessed. To this end, a standard curve was prepared by mixing fully methylated and non-methylated human gDNA for final methylation percentages of 100%, 75%, 50%, 25% and 0% while maintaining a 20 ng/µl total DNA concentration. Percentage methylation values for standards determined by the one-step method coincided closely to actual percent methylation values in both loci (FIG. 5).

Figure 6:
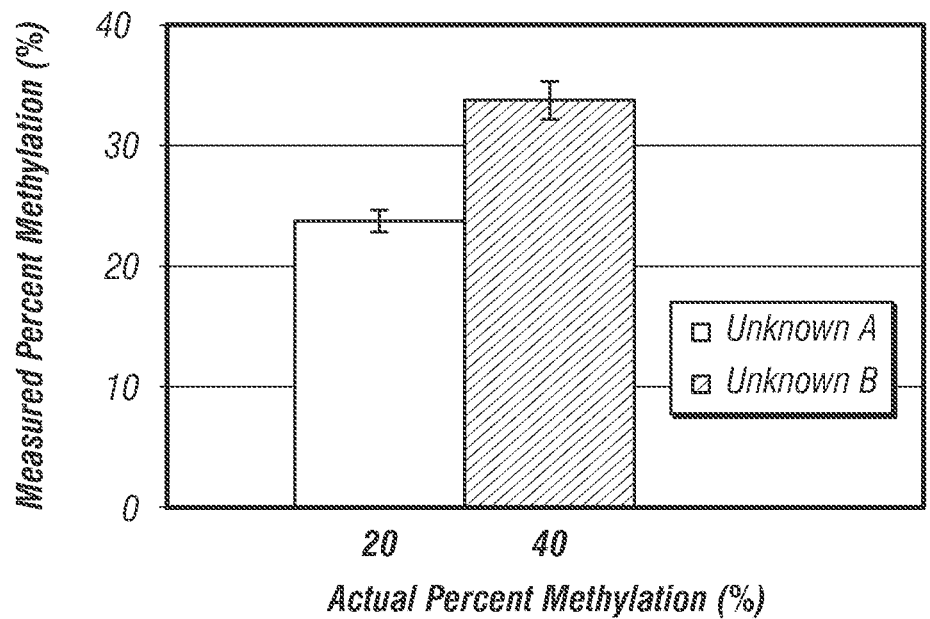
FIG. 6: One-step methylation quantification method accurately determines methylation profiles of blind controls. Two blind controls prepared by mixing fully methylated or non-methylated human DNA with known methylation percentages were subjected to one-step MSE qPCR method. ΔCt values were used to determine methylation values by use of the established relationship. Error bars represent standard deviation.

The one-step system was further validated by identifying methylation percentages of two blind controls prepared by mixing fully methylated or non-methylated human DNA with known methylation percentages. Methylation percentages in the hMSH2 locus determined by the one-step system corresponded closely with the actual methylation percentages (FIG. 6). Together, these data provide a compelling argument for the application of the one-step MSE-qPCR system a cost-efficient, rapid tool for accurately assessing methylation profiles of specific DNA loci.

The present study clearly demonstrates that the one-step MSE-qPCR system accurately quantifies percent methylation. Unmethylated DNA was efficiently digested and allowed for the selective methylated DNA amplification. Further evaluation of the system revealed that it is comparable to qAMP, a procedure which is less time-efficient and involves two separate steps that increase the risk of contamination. An additional advantage of the one-step method over qAMP is that, in a single buffer system, an environment conducive for efficient digestion by multiple MSEs is created. This remarkable hallmark of the one-step system allows for the simultaneous evaluation of CpG dinucleotides within different MSE's cognate sequences. Conversely, employment of a typical buffer system by qAMP restricts which MSEs may be digested within the same reaction tube. Methylation values of standard and blind control samples using one-step quantification method coincided closely with actual methylation values. Thus, this study establishes the value of the one-step MSE-qPCR method in rapid and accurate methylation profiling.

Example 2

Protocol for One-Step DNA Methylation Quantification

The following example protocol uses methylated and non-methylated human DNA standards to demonstrate one-step quantification of methylation using the One-Step qMethyl™ PCR procedure. To determine percent DNA methylation for a given locus, both a test reaction and control reaction are prepared.

I. Preparation of Test and Control Reactions Mixtures

1. The following reactions are prepared on ice for human methylated/non-methylated DNA standards and an appropriate primer set (e.g., the Mgmt Primer set).

Control Reaction

| | |
|---|---|
| 37.5 µl | 2x Control PreMix (5 mM Syto9, 7.5 mM $MgCl_2$, 0.08 U/µl ZymoTaq DNA Polymerase, 2 mM dNTP mix, 0.25 U/µl HpaII, 0.045 U/µl HpyCH4IV, 0.04 U/µl AccII) |
| 3 µl | 10 uM Mgmt Primer I (5'-GGTGTGAAAACTTTGAAGGA-3'; SEQ ID NO: 7) |
| 3 µl | 10 uM Mgmt Primer II (5'-CACTATTCAAATTCCAACCC-3'; SEQ ID NO: 8) |
| 3 µl | human methylated/non-methylated DNA standard (20 ng/µl) |
| 28.5 µl | $ddH_2O$ |
| 75 µl | total volume* |

Test Reaction

| | |
|---|---|
| 37.5 µl | 2x test PreMix |
| 3 µl | 10 µM Mgmt Primer I |
| 3 µl | 10 µM Mgmt Primer II |
| 3 µl | human methylated/non-methylated DNA Standard (20 ng/µl) |
| 28.5 µl | ddH2O |
| 75 µl | total volume* |

* The final concentration of $MgCl_2$ and primers in control reaction and test reactions above is 3.75 mM and 400 nM, respectively.

Human non-methylated DNA standard was purified from HCT116 DKO cells (DNMT1 (−/−)/DNMT3b (−/−)).

Human methylated DNA standard was purified from HCT116 DKO cells (DNMT1 (−/−)/DNMT3b (−/−)) and enzymatically methylated with M.SssI methyltransferase (EC 2.1.1.37).

Both standards were formulated at a concentration of 20 ng/µl in buffer (10 mM Tris-HCl, 1 mM EDTA, pH 8.0) and stored at −20° C.

2. Load 20 µl of the control and test reactions made from non-methylated and methylated human DNA standards as well as any sample DNA onto a real-time qPCR plate in triplicate and secure the plate. To eliminate air bubbles that may be present within the wells, briefly tap or spin down the plate immediately before real-time PCR amplification.

II. MSE Digest and Real-Time PCR Amplification

The following parameters for qPCR (temperatures and times below) have been optimized for digestion and amplification of methylated and non-methylated human DNA standards and can be used as a guideline when setting up qPCR. Using the non-methylated and methylated human DNA standards above and the Mgmt I & II primers the expected amplicon should be 186 bp in length and have the sequence (SEQ ID NO: 9) shown below:

```
-1121
gggtgtgaaa actttgaagg aaaccgcgtc aagagcctgg

-1161
ctgattgtta atatcacgtt aactcagagg gccaggatac

-1201
ttgcccagac ccggagtctg cctgcaagta gcagaggaga

-1251
gctggccttg ctctgccgcg tgtctttctt cctgggccct

-1291
ctgtctcggg ttggaatttg
```

The annealing temperature and extension time for test DNA samples can be adjusted according to primer melting temperatures (Tms) and amplicon size, respectively. Between 35-40 cycles amplification cycles are used for most DNA templates. Typically primers are designed to span a DNA region of 120 bp to 350 bp that comprises at least two sites of potential methylation.

1. Place 96-well plate into a thermal cycler set to an excitation and emission wavelength of 465 and 510 nm, respectively.

2. Perform real-time PCR using. Example parameters are indicated below.

| | Temperature | Time |
|---|---|---|
| Digestion Initial | 37° C. | 2 hours |
| Denaturation | 95° C. | 10 minutes |
| Denaturation* | 94.5° C. | 30 seconds |
| Annealing* | 54° C. | 60 seconds |
| Extension* | 72° C. | 60 seconds |
| Final Extension | 72° C. | 7 minutes |
| Hold | 4° C. | "hold" |

*The Denaturation, Annealing and Extension steps are repeated 35-40 times.

III. Data Analysis

Figure 7:
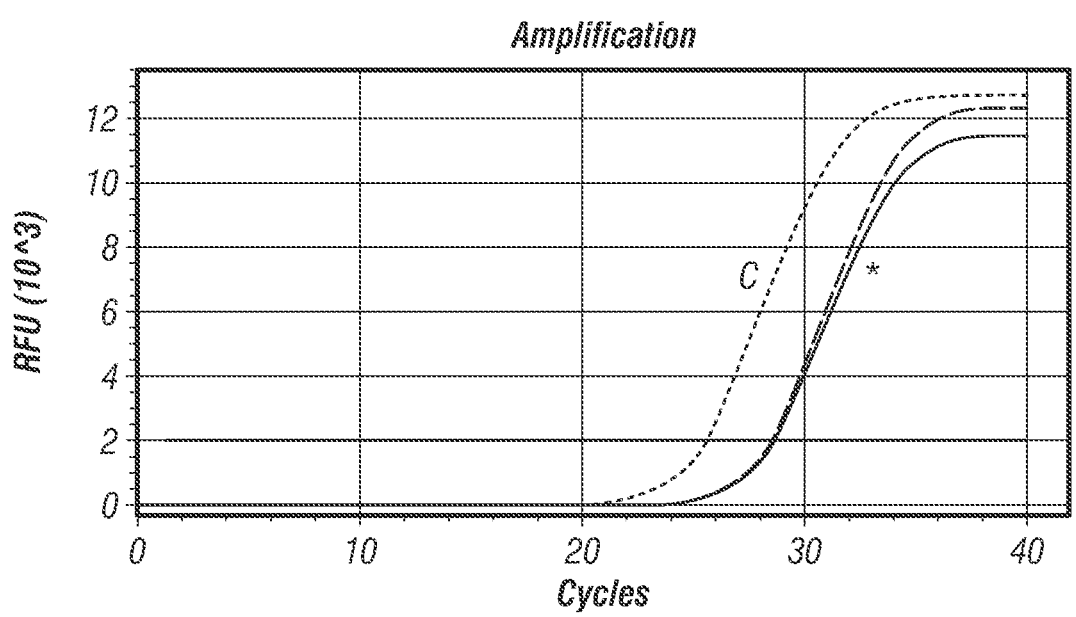
FIG. 7: Amplification curve for a one-step methylation quantification reaction. A non-methylated human DNA standard was subjected to the one-step methylation quantification method using Mgmt I and II (SEQ ID NOs: 7-8) primers for qPCR amplification. The amplification curve revealed significant differences in Ct value between test (*) and control reactions (c), demonstrating not only the efficiency of the test reaction to specifically cleave non-methylated DNA but also the robust real-time amplification that ensues within test and control reactions.
Figure 8:
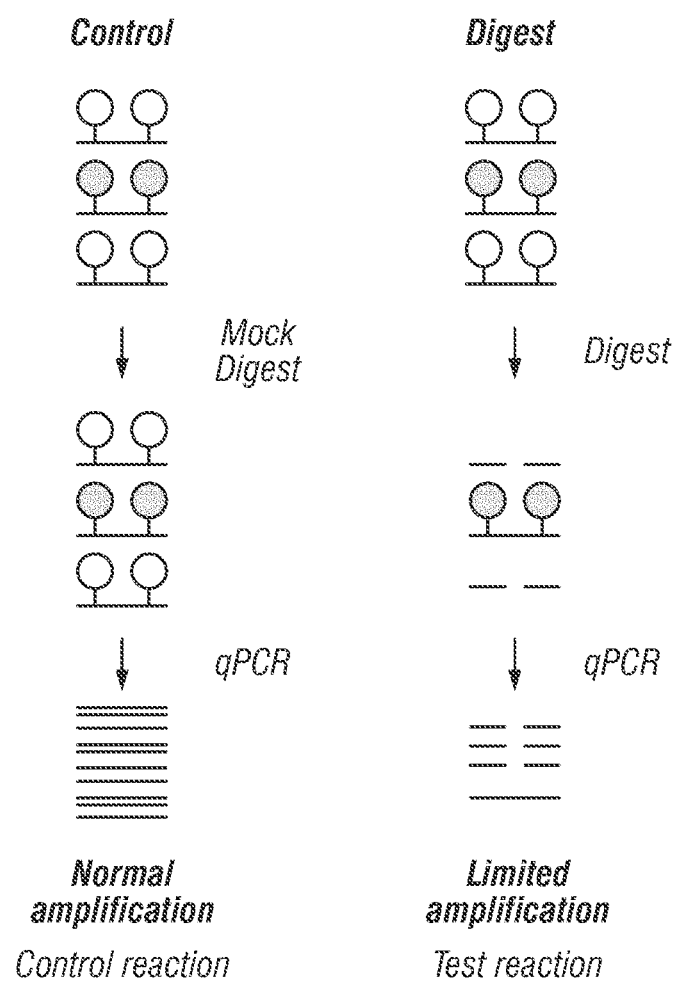
FIG. 8: A schematic diagram illustrating one-step methylation quantification method in a control and test (digest) reaction mix.

1. The percent methylation for the amplified locus can be determined by applying the following equation:

Percent methylation=$100 \times 2^{-\Delta Ct}$ where $\Delta Ct$=average Ct from the test reaction−average Ct control reaction As an example non-methylated DNA samples provided the following results and the amplification curves shown in FIG. 7.

| Ct values of Control Reaction | Ct values of Test Reaction |
|---|---|
| 29.73 | 32.66 |
| 29.70 | 32.80 |
| 29.96 | 32.62 |

1. Calculate the average Ct value of control and test reactions.

| Average Ct value of Control Reaction | Average Ct value of Test Reaction |
|---|---|
| 29.80 | 32.69 |

2. Determine the $\Delta Ct$ by subtracting the average Ct value of test reaction from the average Ct value of control reaction (32.69−29.80=2.90).

3. Plug the $\Delta Ct$ into the equation: $100 \times 2^{-\Delta Ct}$ ($100 \times 2^{-2.90}$=13.4%)

Using the one-step method the actual methylation level of the non-methylated DNA standard was determined to be 13.4%. The actual value has been shown to be around 5%.

Example 3

Procedure for Methylation Quantification at Multiple Loci

Using one-step PCR to detect methylation percentages of multiple loci can be accomplished by formulating reactions mixtures indicated below.

1. Prepare the following master mix where n is the number of loci.

| | |
|---|---|
| n x 37.5 µl | 2x control PreMix |
| n x 3 µl | DNA sample (20 ng/µl) |
| n x 28.5 µl | ddH2O |

2. Dilute primers to 10 µM. Label n PCR tubes with loci names.

3. Aliquot 62.1 µl master mix into n PCR tubes and add 2.7 µl forward and reverse primer for a particular loci to the corresponding tube.

4. Repeat using 2× test PreMix instead of 2× control PreMix.

Continue As indicated in Example 2, step II.

REFERENCES

Each of the foregoing documents is hereby incorporated by reference in its entirety:

U.S. Pat. Nos. 5,436,134 and 5,658,751.
Chernukin et al., *Biotechnologia*, 4:31-25, 2006
Jones and Laird, *Nat. Genet.*, 21(2):163-7, 1999.
Oakes et al., *Epigenetics*, 1(3):146-152, 2009.
Russian Patent No. 2322494.
Sambrook et al.; *In: Molecular Cloning-A Laboratory Manual* (second edition), Cold Spring Harbour Laboratory Press, 1989.
Sutherland et al., *J. Mol. Biol.*, 225:327-334, 1992.

The invention claimed is:

1. A method for quantitating a proportion of methylation of a DNA sequence in a DNA sample comprising:
   (i) contacting the DNA sample with a premixture comprising three methylation-sensitive endonucleases (MSEs), a thermal stable DNA polymerase, oligonucleotide primers for amplifying the DNA sequence, and a buffer formulated to facilitate activity of the MSEs and the DNA polymerase, thereby forming a reaction mixture, wherein the MSEs consist of AccII, HpaII, and HpyCH4IV;
   (ii) incubating the reaction mixture under conditions permissive for cleaving the DNA sequence by the MSEs;
   (iii) after step (ii), producing an amplified product by incubating the reaction mixture under conditions permissive for quantitative polymerase chain reaction (PCR); and
   (iv) quantitating the proportion of methylation in the DNA sequence of the DNA sample by quantitating the amplified product,
   wherein the volume of the reaction mixture is not adjusted during steps (ii)-(iii).

2. The method of claim 1, wherein the MSEs are enzymes that do not cleave DNA at CpG methylated positions.

3. The method of claim 1, wherein the DNA polymerase is a thermophilic polymerase.

4. The method of claim 1, wherein the premixture further comprises a hot-start DNA polymerase.

5. The method of claim 1, wherein said quantitating the proportion of methylation in the DNA sequence of the DNA sample comprises comparing the amount of the amplified product to an amplification standard, wherein the amplification standard is a DNA sample with a known proportion of methylation and a known amount.

6. The method of claim 1, wherein the oligonucleotide primers comprise a label.

7. The method of claim 1, wherein the premixture further comprises an oligonucleotide probe that hybridizes to the DNA sequence and comprises a label.

8. The method of claim 7, wherein the label is a fluorescent label, a radioactive label, a sequence label, an enzymatic label or an affinity label.

9. The method of claim 1, wherein the premixture comprises free nucleotides that comprise a label or a label that binds to a double-stranded DNA.

10. The method of claim 9, wherein step (iv) further comprises detecting the label.

11. The method of claim 1, wherein the DNA sample is a mammalian genomic DNA sample.

12. The method of claim 11, wherein the mammalian genomic DNA sample is from a human subject, a cell line, or a tissue bank.

13. The method of claim 11, wherein the mammalian genomic DNA sample is from a blood sample, a tissue biopsy sample, a urine sample, or a saliva sample.

14. The method of claim 1, wherein the thermal stable DNA polymerase is a Taq polymerase.

\* \* \* \* \*

SEQUENCE LISTING

<160> NUMBER OF SEQ ID NOS: 9

<210> SEQ ID NO 1
<211> LENGTH: 20
<212> TYPE: DNA
<213> ORGANISM: Artificial Sequence
<220> FEATURE:
<223> OTHER INFORMATION: Synthetic primer

<400> SEQUENCE: 1
gcttcgtgcg cttctttcag                                               20

<210> SEQ ID NO 2
<211> LENGTH: 20
<212> TYPE: DNA
<213> ORGANISM: Artificial Sequence
<220> FEATURE:
<223> OTHER INFORMATION: Synthetic primer

<400> SEQUENCE: 2
ccgtgcgccg tatagaagtc                                               20

<210> SEQ ID NO 3
<211> LENGTH: 21
<212> TYPE: DNA
<213> ORGANISM: Artificial Sequence
<220> FEATURE:
<223> OTHER INFORMATION: Synthetic probe

<400> SEQUENCE: 3
catgccggag aagccgacca c                                             21

<210> SEQ ID NO 4
<211> LENGTH: 21
<212> TYPE: DNA
<213> ORGANISM: Artificial Sequence
<220> FEATURE:
<223> OTHER INFORMATION: Synthetic primer

<400> SEQUENCE: 4
tcatgaccgt gttcaggcag g                                             21

<210> SEQ ID NO 5
<211> LENGTH: 23
<212> TYPE: DNA
<213> ORGANISM: Artificial Sequence
<220> FEATURE:
<223> OTHER INFORMATION: Synthetic primer

<400> SEQUENCE: 5
atgcatttcc acaatccagg agg                                           23

<210> SEQ ID NO 6
<211> LENGTH: 25
<212> TYPE: DNA
<213> ORGANISM: Artificial Sequence
<220> FEATURE:
<223> OTHER INFORMATION: Synthetic probe

<400> SEQUENCE: 6
attactacga caccggcgag gaact                                         25

<210> SEQ ID NO 7
<211> LENGTH: 20
<212> TYPE: DNA
<213> ORGANISM: Artificial Sequence

```
<220> FEATURE:
<223> OTHER INFORMATION: Syntheic primer

<400> SEQUENCE: 7
ggtgtgaaaa ctttgaagga                                              20

<210> SEQ ID NO 8
<211> LENGTH: 20
<212> TYPE: DNA
<213> ORGANISM: Artificial Sequence
<220> FEATURE:
<223> OTHER INFORMATION: Synthetic primer

<400> SEQUENCE: 8
cactattcaa attccaaccc                                              20

<210> SEQ ID NO 9
<211> LENGTH: 180
<212> TYPE: DNA
<213> ORGANISM: Homo sapiens

<400> SEQUENCE: 9
gggtgtgaaa actttgaagg aaaccgcgtc aagagcctgg ctgattgtta atatcacgtt   60
aactcagagg gccaggatac ttgcccagac ccggagtctg cctgcaagta gcagaggaga  120
gctggccttg ctctgccgcg tgtctttctt cctgggccct ctgtctcggg ttggaatttg  180
```